US012082787B2

(12) United States Patent
Inglis et al.

(10) Patent No.: US 12,082,787 B2
(45) Date of Patent: Sep. 10, 2024

(54) VIDEO LARYNGOSCOPE SYSTEMS AND METHODS

(71) Applicant: Covidien AG, Neuhausen am Rheinfall (CH)

(72) Inventors: Peter Douglas Colin Inglis, Boulder, CO (US); Matthew John Ross McGrath, New York, NY (US); Michael Ng, Kowloon (HK)

(73) Assignee: Covidien AG (CH)

( * ) Notice: Subject to any disclaimer, the term of this patent is extended or adjusted under 35 U.S.C. 154(b) by 403 days.

(21) Appl. No.: 17/315,594

(22) Filed: May 10, 2021

(65) Prior Publication Data
US 2021/0259536 A1 Aug. 26, 2021

Related U.S. Application Data

(63) Continuation of application No. 16/174,026, filed on Oct. 29, 2018, now Pat. No. 11,033,180.
(Continued)

(51) Int. Cl.
| | |
|---|---|
| *A61B 1/267* | (2006.01) |
| *A61B 1/00* | (2006.01) |
| *A61B 1/05* | (2006.01) |
| *A61B 1/06* | (2006.01) |
| *A61M 16/04* | (2006.01) |

(Continued)

(52) U.S. Cl.
CPC .......... *A61B 1/267* (2013.01); *A61B 1/00016* (2013.01); *A61B 1/0005* (2013.01); *A61B 1/00052* (2013.01); *A61B 1/00105* (2013.01); *A61B 1/05* (2013.01); *A61M 16/0495* (2014.02); *A61B 1/00027* (2013.01); *A61B 1/00048* (2013.01); *A61B 1/00066* (2013.01); *A61B 1/0051* (2013.01); *A61B 1/0676* (2013.01); *A61B 1/0684* (2013.01); *A61B 90/90* (2016.02); *A61B 90/98* (2016.02); *A61B 2562/08* (2013.01);
(Continued)

(58) Field of Classification Search
CPC ....... A61B 1/267; A61B 1/00052; A61B 1/05; A61B 1/0684
See application file for complete search history.

(56) References Cited

U.S. PATENT DOCUMENTS

| | | |
|---|---|---|
| 5,529,570 A | 6/1996 | Storz |
| 7,568,619 B2 | 8/2009 | Todd et al. |

(Continued)

FOREIGN PATENT DOCUMENTS

| | | |
|---|---|---|
| WO | 2011/141686 | 11/2011 |
| WO | 2018/136905 | 7/2018 |

OTHER PUBLICATIONS

EP Office Action for EP Application No. 18 800 290.1 mailed Nov. 4, 2022 (4 pages).

(Continued)

*Primary Examiner* — Tracy L Kamikawa

(57) ABSTRACT

A laryngoscope system includes a body having a handle and an arm, a camera mounted on a distal end of the arm, and a removable blade having a channel sized to fit over the arm to couple the blade to the body. The blade includes a magnet, and a sensor disposed in the body is responsive to the magnet. The laryngoscope system also includes a processor disposed in the body and programmed to enable at least one monitoring function in response to a signal from the sensor.

8 Claims, 7 Drawing Sheets

Related U.S. Application Data

(60) Provisional application No. 62/581,461, filed on Nov. 3, 2017.

(51) Int. Cl.
*A61B 1/005* (2006.01)
*A61B 90/90* (2016.01)
*A61B 90/98* (2016.01)

(52) U.S. Cl.
CPC ............... *A61M 2205/3569* (2013.01); *A61M 2205/3592* (2013.01); *A61M 2205/505* (2013.01)

(56) References Cited

U.S. PATENT DOCUMENTS

| | | | |
|---|---|---|---|
| 8,055,830 | B2 | 11/2011 | Waldhoff et al. |
| 8,194,122 | B2 | 6/2012 | Amling et al. |
| 8,634,031 | B2 | 1/2014 | Ikeda |
| 8,652,033 | B2 | 2/2014 | Berci et al. |
| 8,746,239 | B2 | 6/2014 | Yoshida |
| 8,982,199 | B2 | 3/2015 | Amling et al. |
| 9,033,895 | B2 | 5/2015 | Furlong et al. |
| 9,473,749 | B2 * | 10/2016 | Selby .................... H04N 7/183 |
| 9,538,908 | B2 | 1/2017 | Allyn et al. |
| 10,149,957 | B2 | 12/2018 | Runnels |
| 10,307,599 | B2 | 6/2019 | Schilling |
| 2006/0247606 | A1 | 11/2006 | Batch |
| 2007/0167686 | A1 * | 7/2007 | McGrath ............. H05K 999/99 600/188 |
| 2009/0187078 | A1 * | 7/2009 | Dunlop .................... A61B 1/07 600/179 |
| 2011/0130632 | A1 * | 6/2011 | McGrail ............ G02B 23/2446 600/188 |
| 2012/0246184 | A1 * | 9/2012 | Rothschild ......... H04N 1/00946 707/E17.014 |
| 2013/0204085 | A1 * | 8/2013 | Alexander ......... A61B 1/00158 600/101 |
| 2013/0237763 | A1 | 9/2013 | Qui |
| 2014/0266577 | A1 | 9/2014 | Anderson et al. |
| 2015/0080655 | A1 | 3/2015 | Peterson et al. |
| 2016/0120394 | A1 | 5/2016 | McGrath et al. |
| 2016/0279365 | A1 | 9/2016 | Esnouf |
| 2017/0215720 | A1 | 8/2017 | Walker et al. |
| 2018/0338675 | A1 * | 11/2018 | Eggli .................... A61B 1/267 |

OTHER PUBLICATIONS

Ambu_aScope_3_Large_Brochure_4963605, Oct. 2017.
Rothfield, K., "The Video Laryngoscopy Market_Past Present and Future," Anesthesiology News Guide to Airway Management 2014.
Siena, F.L., et al., "The development of a novel steerable bougie to assist in airway management," AMJ 2016; 9 (5):124-137.
Sowers, N., et al., "Use of a Flexible Intubating Scope in Combination with a Channeled Video Laryngoscope for Managing a Difficult Airway in the Emergency Department," The Journal of Emergency Medicine, vol. 50, No. 2, pp. 315-319, 2016.
Weissbrod, P.A., et al., "Reducing Injury During Video-Assisted Endotracheal Intubation: The "Smart Stylet" Concept," Laryngoscope, 121:2391-2393, 2011.
AU Examination Report for AU Application No. 2018361822 mailed Sep. 6, 2023 (4 pages).

* cited by examiner

VIDEO LARYNGOSCOPE SYSTEMS AND METHODS

CROSS-REFERENCE TO RELATED APPLICATIONS

The present application is a continuation of U.S. application Ser. No. 16/174,026, entitled "VIDEO LARYNGOSCOPE SYSTEMS AND METHODS" and filed Oct. 29, 2018, issued as U.S. Pat. No. 11,033,180, on Jun. 15, 2021, which claims priority to and the benefit of U.S. Provisional Application No. 62/581,461, entitled "VIDEO LARYNGOSCOPE SYSTEMS AND METHODS" and filed Nov. 3, 2017. These applications are hereby incorporated by reference in their entireties for all purposes.

BACKGROUND

The present disclosure relates generally to medical devices and, more particularly, to video laryngoscope systems and methods.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during mechanical ventilation. Such tracheal tubes may include endotracheal (ET) tubes, tracheostomy tubes, or transtracheal tubes. Laryngoscopes are in common use for the insertion of endotracheal tubes into the tracheas of patients during medical procedures. Laryngoscopes may include a light source to permit visualization of the patient's airway to facilitate intubation, and video laryngoscopes may also include an imager, such as a camera. A laryngoscope, when in use, extends only partially into the patient's airway, and the laryngoscope may function to push the patient's tongue aside to permit a clear view into the airway for insertion of the endotracheal tube.

SUMMARY

Certain embodiments are summarized below. These embodiments are not intended to limit the scope of the disclosure. Indeed, the present disclosure may encompass a variety of forms that may be similar to or different from the embodiments set forth below.

In one embodiment, a laryngoscope system includes a body having a handle and an arm, a camera mounted on or near a distal end of the arm, and a removable blade having a channel sized to fit over the arm to couple the blade to the body. The blade includes a magnet, and a sensor disposed in the body is responsive to the magnet. The laryngoscope system also includes a processor disposed in the body and programmed to enable at least one monitoring function in response to a signal from the sensor.

In one embodiment, a laryngoscope includes a handle, an elongate portion extending from the handle, a camera mounted on or near a distal end of the elongate portion, and a sensor carried by the elongate portion and responsive to generate a signal in response to detection of an activating element positioned proximate the sensor. The laryngoscope also includes a processor configured to enable at least one added monitoring function in response to receipt of the signal from the sensor.

In one embodiment, a method of operating a video laryngoscope system includes detecting, using a sensor, an activating element coupled to an activating blade positioned about an elongate portion of a video laryngoscope. The method also includes generating, using the sensor, a signal in response to detection of the activating element. The method further includes enabling, using a processor, advanced monitoring functions of the video laryngoscope in response to receipt of the signal from the sensor.

In one embodiment, a laryngoscope blade includes an activating element for sensing by a sensor provided in a laryngoscope thereby to activate at least one monitoring function. In another embodiment, a set of laryngoscope blades is provided, whereby each blade includes a respective activating element for sensing by a sensor, the activating elements being of different type or configuration or each having at least one different property thereby to activate different monitoring function(s) of a laryngoscope. A blade or a set of blades as provided herein may include an activating element(s) including at least one of a magnet, an optical element, an RFID tag, a visible marker, or a switch-actuating feature.

Features in one aspect or embodiment may be applied as features in any other aspect or embodiment, in any appropriate combination. For example, any one of system, blade or method features may be applied as any one or more other of system, blade or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
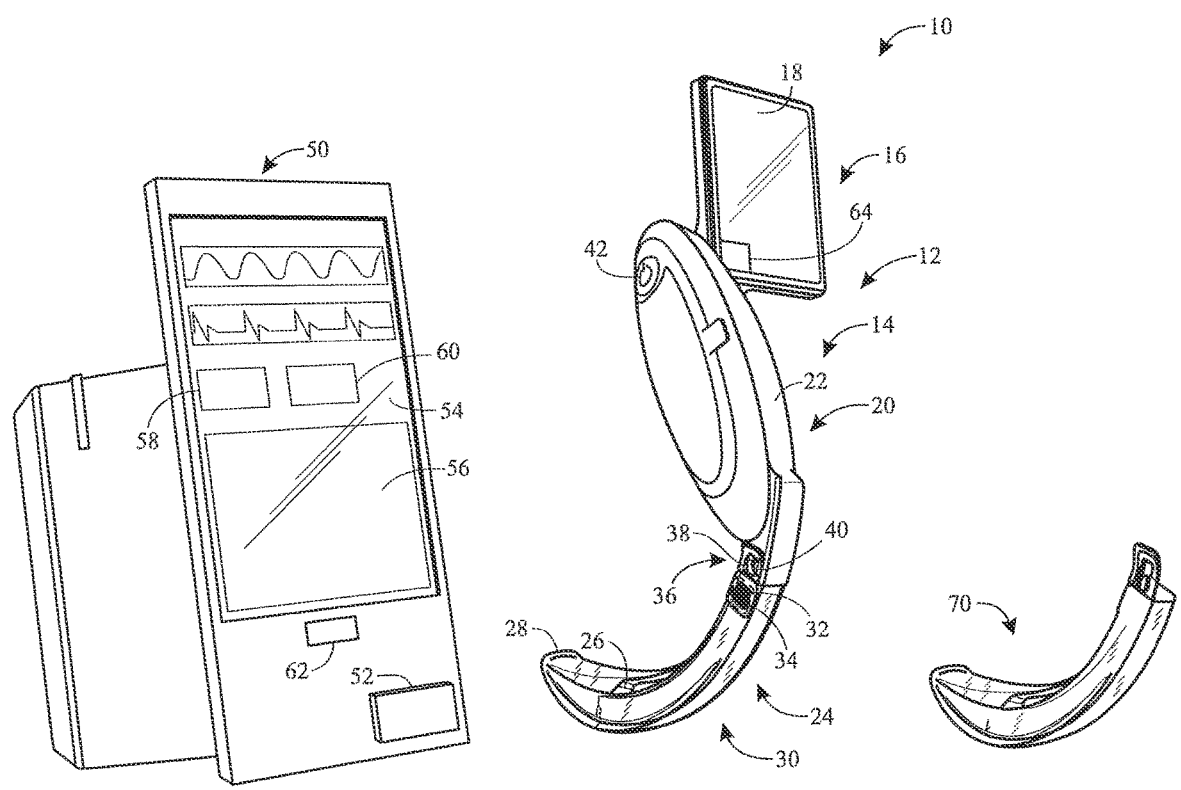
FIG. 1 is a perspective view of a laryngoscope system having a laryngoscope, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A medical professional may use a laryngoscope to view a patient's oral cavity to facilitate insertion of a tracheal tube (e.g., endotracheal tube, tracheostomy tube, or transtracheal tube) into the patient's trachea. Certain laryngoscopes may provide an indirect view of the patient's oral cavity via prisms, lenses, reflective surfaces, or the like. However, in some cases, it may be desirable to position a camera on a portion of the laryngoscope that is inserted into the patient's oral cavity to obtain an image (e.g., still image and/or moving image, such as a video) of the oral cavity. The image may then be displayed during the intubation procedure to enable the medical professional to visualize the oral cavity and to facilitate insertion of the tracheal tube, for example. Accordingly, the disclosed embodiments generally relate to a video laryngoscope system that includes a laryngoscope with a body (e.g., reusable body) having an elongate portion (e.g., a camera stick) that supports a camera, a display portion with a display screen that is configured to display an image obtained by the camera, and a handle portion with a handle that is configured to be gripped by the medical professional during the laryngoscopy procedure. In some embodiments, a blade for the laryngoscope is provided as a removable cover (e.g., disposable, reusable, or reprocessable cover or sleeve) that fits over the elongate portion of the body of the laryngoscope. Together, the blade and the elongate portion of the body may form an insertable assembly that is configured to be inserted into and to manipulate the patient's oral cavity.

Additionally, in certain clinical settings, such as in an emergency situation, it may be beneficial to operate the laryngoscope in a relatively simple, uncomplicated manner, without advanced monitoring functions, in order to quickly intubate the patient. In certain clinical settings, such as in an operating room or when intubating a patient with atypical anatomy or a complex medical condition, it may be beneficial to operate the laryngoscope with relatively advanced monitoring functions (e.g., additional and/or different monitoring functions) and/or to coordinate the use of the laryngoscope with other medical devices (e.g., monitors, hospital data storage systems, or the like). Advantageously, the disclosed embodiments may provide a versatile laryngoscope system that is configured to selectively vary its monitoring functions (e.g., to selectively perform advanced monitoring functions) in different clinical settings.

In some embodiments, the laryngoscope system is configured to vary its monitoring functions based on detection of an activating element (e.g., magnet) by a sensor positioned on the body of the laryngoscope. For example, the advanced monitoring functions of the laryngoscope system may be enabled in response to detection of the activating element by the sensor. In some embodiments, the activating element may be coupled to the removable blade that is attached to the elongate portion of the body of the laryngoscope. Thus, in such cases, the laryngoscope system is configured to vary its monitoring functions based on a type of blade coupled to the body of the laryngoscope. For example, when one type of blade (e.g., basic or non-activating blade) that is devoid of the activating element is coupled to the body of the laryngoscope, the laryngoscope enables basic functionality, such as obtaining images using the camera and displaying the images on the display portion of the laryngoscope to enable the medical professional to view the oral cavity during the laryngoscopy procedure. However, when another type of blade (e.g., advanced or activating blade) having the activating element is coupled to the body of the laryngoscope, the laryngoscope may obtain images using the camera, display the images on the display portion of the laryngoscope, and also enable additional monitoring functions (e.g., advanced monitoring functions), such as recording of data (e.g., images, time data, or the like) on a memory of the laryngoscope and/or transfer of data to another device (e.g., a monitor, hospital data storage systems, or the like). For example, in some embodiments, the laryngoscope enables wireless streaming of video images to a monitor in real-time during the laryngoscopy procedure in response to detection of the activating element.

It should be appreciated that the relatively basic functions and the relatively advanced monitoring functions disclosed herein may include any of a variety of functions and refer to different sets of functions (e.g., a first set of functions and a second set of functions) that are selectively enabled based on whether a sensor of the laryngoscope detects the presence of the activating element, which may be coupled to the blade. The functions that are enabled may include one or more of the following: obtaining images using the camera, providing the images for display on the display portion, recording of data on a memory of the laryngoscope, transfer of data to another device (e.g., streaming or automatic transfer at various times), and any of a variety of other monitoring functions. The relatively basic or default functions (e.g., of a default mode of operation) are carried out in the absence of detection of the activating element, while the relatively advanced monitoring functions (e.g., of an advanced monitoring mode of operation) are enabled in response to detection of the activating elements. The relatively basic or default functions may include one or more of the above-listed functions, while the relatively advanced monitoring functions may be different (e.g., a different set or combination of functions) than the relatively basic functions; and/or may add to, augment, or enhance the relatively basic functions. As discussed in more detail below, the laryngoscope may be utilized with multiple different types of blades having various different activating elements that may enable various different monitoring functions (e.g., different sets of functions, such as a third set of functions, a fourth set of functions, and so on).

With the foregoing in mind, FIG. 1 is a perspective view of an embodiment of a laryngoscope system 10. As shown, the laryngoscope system 10 includes a laryngoscope 12 having a body 14 (e.g., reusable body) with a display portion 16 having a display screen 18 that is configured to display images or other data, a handle portion 20 having a handle 22 that is configured to be gripped by the medical professional during the laryngoscopy procedure, and an elongate portion or arm 24 that supports a camera 26 that is configured to obtain images (e.g., still images and/or moving images, such as videos). It should be appreciated that the display portion 16 and the handle portion 20 may not be distinct portions, such that the display screen 18 is integrated into the handle portion 20. In the illustrated embodiment, an activating cover, such as a removable laryngoscope blade 28 (e.g., activating blade; disposable cover, sleeve, or blade), is positioned about the arm 24 of the body 14 of the laryngoscope 12. Together, the arm 24 of the body 14 and the blade 28 form an insertable assembly 30 that is configured to be inserted into the patient's oral cavity. It should be appreciated that the display portion 16, the handle portion 20, and/or the arm 24 that form the body 14 of the laryngoscope 12 may be fixed to one another or integrally formed with one another (e.g., not intended to be separated by the medical professional during routine use) or may be removably coupled to one another (e.g., intended to be separated by the medical professional during routine use) to facilitate storage, use, inspection, maintenance, repair, cleaning, replacement, or interchangeable parts (e.g., use of different arms or extensions with one handle portion 20), for example. In one embodiment, the arm 24 is configured as a camera stick that includes a housing, rod, shaft, or support structure that carries the camera 26 and a light source, such as a light emitting diode (LED). The arm 24 may be a generally rigid structure (e.g., the arm 24 may be configured as a camera stick with a rigid support structure), or the arm 24 may be a generally flexible or semi-flexible structure (e.g., the arm 24 may be configured as a camera stick with a flexible or semi-flexible support structure). It should be appreciated that the arm 24 may be devoid the light source and/or the light source may be provided as part of the camera 26 or on the blade 28.

As discussed in more detail below, the blade 28 may include an activating element that is configured to interact with the body 14 of the laryngoscope 12 to activate or enable certain monitoring functions (e.g., different, additional, and/or advanced monitoring functions). In the illustrated embodiment, the activating element includes a magnet 32 coupled to the blade 28. In operation, when the blade 28 is positioned on the arm 24 of the body 14, the magnet 32 may be detected by a sensor 34 (e.g., magnetometer, proximity sensor, reed switch, Hall effect sensor) disposed within or coupled to any suitable location of the body 14. For example, in the illustrated embodiment, the sensor 34 is positioned in the arm 24, such that the magnet 32 covers or overlays the sensor 34 when the blade 28 is coupled to the body 14. It should be appreciated that the blade 28 and the body 14 of the laryngoscope 12 may be configured to facilitate various magnetic interactions. Thus, the magnet 32 disclosed herein may also refer to a magnetically-responsive material (e.g., a piece of iron), and in such cases, the sensor 34 may be a magnetic sensor that is responsive to the magnetically-responsive material and/or that enables differentiation between different sizes of magnetically-responsive materials. As discussed in more detail below, it should be appreciated that the activating element may include any of a variety of devices or structures, and the body 14 may include any of a variety of sensors configured to detect the activating element to enable the advanced monitoring functions. In some cases, the sensor may include a basic sensor or mechanical switch that changes its state when the activating element is proximate to the sensor. Furthermore, in some embodiments, the position of the sensor 34 and the magnet 32 may be changed or exchanged.

As shown, the blade 28 and the body 14 are coupled to one another via a coupling 36 (e.g., key-slot interface, prong, fastener, interference fit, adhesive, suction, or the like). In the illustrated embodiment, the blade 28 includes a slot 38 (e.g., opening or recess) that receives a key 40 (e.g., protrusion or prong) of the body 14 (e.g., on the handle or arm), thereby coupling the blade 28 to the body 14. However, it should be understood that in other embodiments, the slot 38 may be formed in the body 14, and the key 40 may be provided on the blade 28. The laryngoscope 12 may also include a power button 42 that enables a medical professional to power the laryngoscope 12 off and on. In the illustrated embodiment, the laryngoscope 12 includes an input button, such as a touch or proximity sensor 64 (e.g., capacitive sensor, proximity sensor, or the like) that is configured to detect an object (e.g., a finger or stylus). The touch sensor 64 may enable the medical professional operating the laryngoscope 12 to efficiently provide inputs or commands, such as inputs that cause the camera 26 to obtain or store an image on a memory of the laryngoscope.

As discussed in more detail below, in response to detection of the magnet 32 by the sensor 34 of the body 14 of the laryngoscope 12 (i.e., after the magnet 32 is brought into proximity of the sensor 34 when the blade 28 is coupled to the body 14 of the laryngoscope 12), the laryngoscope system 10 may enable advanced monitoring functions, such as recording data on a memory of the laryngoscope 12 and/or transmitting data from the laryngoscope 12 to one or more remote devices or systems, such as a monitor 50 (e.g., remote monitor), a computing system, and/or a hospital data storage system. For example, in an embodiment, in response to detection of the magnet 32 by the sensor 34, the laryngoscope 12 records images locally (e.g., in a storage device housed in the body 14) for later access, viewing, or transfer to the monitor 50. In certain embodiments, in response to detection of the magnet 32 by the sensor 34, the laryngoscope 12 communicates with the monitor 50 and/or transmits data (e.g., wirelessly stream images in substantially real-time) to the monitor 50. In certain embodiments, in response to detection of the magnet 32 by the sensor 34, the laryngoscope 12 automatically transmits data from the storage device of the laryngoscope 12 to the monitor 50 and/or transmits data to one or more other remote devices or systems at certain times (e.g., upon powering the laryngoscope 12 and/or the monitor 50 off or on, periodically during the laryngoscopy procedure, upon receipt of a user input, upon receipt of an input indicating that the laryngoscopy procedure is complete and/or that certain steps of the laryngoscopy procedure are complete).

The laryngoscope 12 may be configured to communicate with the monitor 50 and/or other remote devices or systems via any of a variety of techniques. For example, the laryngoscope 12 and the monitor 50 may include communication devices (e.g., wireless transceivers) that are configured to establish wireless communication with one another using any suitable protocol. In the illustrated embodiment, an adapter 52 (e.g., wireless adapter, dongle, or bridge device) is provided to facilitate wireless communication between the laryngoscope 12 and the monitor 50 and/or other remote devices and systems. For example, in the illustrated embodiment, the adapter 52 includes a wireless transceiver that sends information to and receives information from the laryngoscope 12. The adapter 52 is coupled to the monitor 50 (e.g., by plugging the adapter 52 into a Universal Serial Bus [USB] port of the monitor 50) to relay information or commands between the laryngoscope 12 and the monitor 50. Such a configuration may enable use of the laryngoscope 12 with third-party monitors or multi-parameter monitors. For example, the adapter 52 may be coupled to a first monitor 50 to enable wireless communication (e.g., transfer of video, image, or device status data between the laryngoscope 12 and the monitor 50, transfer of an instruction from the monitor 50 to the laryngoscope 12 to obtain a photo using the camera 26, or the like) between the laryngoscope 12 and the first monitor 50, and the adapter 52 may then be removed from the first monitor 50 and coupled to a second monitor 50 to enable wireless communication between the laryngoscope 12 and the second monitor 50. Thus, the laryngoscope 12 may be configured to communicate with (e.g., transfer data to) a receiver, which may be the monitor 50 or the adapter 52, for example.

As shown, the monitor 50 includes a display screen 54 (e.g., touchscreen display) that is configured to provide information to the medical professional and/or that is configured to receive inputs. For example, the monitor 50 may provide a still or moving image 56 obtained by the camera 26 of the laryngoscope 12, and in some cases, may also provide information obtained via various physiological sensors (e.g., heart rate, oxygen saturation, or the like). In some embodiments, the image 56 may be a video that is streamed wirelessly in substantially real-time from the laryngoscope 12 to the monitor 50. The laryngoscope 12 and the monitor 50 may interact to carry out various other advanced monitoring functions, such as transfer of data (e.g., images, time data, or the like) from the laryngoscope 12 to the monitor 50 in response to an input received (e.g., a touch input from the user at the laryngoscope 12 and/or at the monitor 50) and/or automatic transfer of data from the laryngoscope 12 to the monitor 50 at certain times (e.g., upon powering the laryngoscope 12 and/or the monitor off or on, periodically during the laryngoscopy procedure, upon receipt of a user input, upon receipt of an input indicating that the laryngoscopy procedure is complete and/or that certain steps of the laryngoscopy procedure are complete). For example, in the illustrated embodiment, the monitor 50 includes an input 58 (e.g., virtual button on the display screen 54) that may enable the medical professional to instruct the laryngoscope 12 to stop recording and/or stop transmitting to the monitor 50, and an input 60 (e.g., virtual button on the display screen 54) that may enable the medical professional to instruct the laryngoscope 12 to capture and/or transmit a single still image obtained by the camera 26. The monitor 50 may include various other features, such as a power button 62 that enables a user to power the monitor 50 off and on. It should be appreciated that the laryngoscope 12 and the monitor 50 may also include ports (e.g., USB ports, Ethernet ports, high-definition multimedia interface [HDMI] ports, optical ports, infrared ports, near field ports, or the like) that enable the components to be coupled to one another and/or to other components (e.g., computing systems or storage systems) via a wired connection.

In some embodiments, the display screen 54 of the monitor 50 and/or the display screen 18 of the laryngoscope 12 may be configured to provide an indication that the monitor 50 and the laryngoscope 12 are communicatively coupled to one another. In some embodiments, the laryngoscope 12 may be configured to provide a laryngoscope ID (e.g., numerical or descriptive identifier) to the monitor 50, and the monitor 50 is configured to display the laryngoscope ID on the display screen 54 to enable the medical professional to confirm that the monitor 50 is receiving data from the appropriate laryngoscope 12. In an embodiment, the monitor 50 is configured to connect to only one laryngoscope 12 at a time. In another embodiment, the monitor 50 may connect to two or more laryngoscopes 12, and the user may select (e.g., by touch input on the monitor screen 54) the laryngoscope 12 from which to display images or transfer data. Additionally or alternatively, in some embodiments, the monitor 50 may be configured to provide a monitor ID (e.g., numerical or descriptive identifier) to the laryngoscope 12, and the laryngoscope 12 is configured to display the monitor ID on the display screen 18 to enable the medical professional to confirm that the laryngoscope 12 is transferring data to the appropriate monitor 50. In some embodiments, the monitor 50 and/or the laryngoscope 12 may enable the medical professional to provide inputs (e.g., via one or more touchscreen display screens 18, 54) to adjust or to select the appropriate device(s) (e.g., the monitor 50 and the laryngoscope 12) that should communicate with one another during the laryngoscopy procedure. It should be appreciated that the medical professional may provide various inputs disclosed herein via a voice command to a microphone of the laryngoscope 12. Such configurations may be particularly useful when the laryngoscope system 10 is used in an environment or circumstance in which multiple monitors 50 and/or multiple laryngoscopes 12 are operating simultaneously, for example.

As noted above, the laryngoscope 12 may also be utilized with a non-activating blade 70 (e.g., disposable cover, sleeve, or blade) that does not include the magnet 32 or other activating element. When the non-activating blade 70 is coupled to the body 14 of the laryngoscope 12, the sensor 34 does not detect a magnet, and thus, the advanced monitoring functions are not activated or enabled by the laryngoscope system 10. In such cases, the laryngoscope 12 may provide only relatively basic functionality, thereby providing a relatively low-cost and/or easy-to-operate system. For example, with the non-activating blade 70 coupled to the body 14, the laryngoscope 12 may provide an image or video obtained by the camera 26 on the display 16 of the laryngoscope 12, but may not transfer the image or video to the monitor 50 and/or may not record the image or video locally on the laryngoscope 12.

In some embodiments, the laryngoscope system 10 may be configured to maintain performance of the advanced monitoring functions for the time period between detection of the magnet 32 and powering off the laryngoscope 12. A processor of the laryngoscope 12 may be programmed to maintain the monitoring functions even after a loss of a signal from the sensor 34. For example, in operation, the medical professional may power the laryngoscope 12 on via the power button 42, then the medical professional may select a first activating blade 28 (e.g., based on the estimated appropriate size or shape for the patient), position the first blade 28 on the body 14 of the laryngoscope 12 to activate the advanced monitoring functions, and begin the laryngoscopy procedure. However, in some cases, the medical professional may determine that the first blade 28 is inappropriate (e.g., an incorrect size) for the patient, and the medical professional may then remove the laryngoscope 12 from the patient's oral cavity, select a second activating blade 28 or a non-activating blade 70 (e.g., having the appropriate size or shape for the patient), position the second activating blade 28 or the non-activating blade 70 on the body 14 of the laryngoscope 12, and then resume the laryngoscopy procedure. Maintaining performance of the advanced monitoring functions after positioning the first blade 28 on the body 14 of the laryngoscope 12 may advantageously provide uninterrupted monitoring, data collection and transfer, even while the medical professional changes the blade of the laryngoscope 12 (e.g., changes between different activating blades 28 and/or changes between an activating blade 28 and an appropriately sized or shaped non-activating blade 70). In some embodiments, the laryngoscope 12 may reset when powered off, such that upon subsequently powering the laryngoscope 12 on, the laryngoscope 12 operates with the relatively basic monitoring functions until the sensor 34 detects the magnet 32 (e.g., the original magnet 32 or the magnet 32 of a subsequent blade 28). In some embodiments, the laryngoscope system 10 may be configured to enable the advanced monitoring functions only while the activating blade 28 is coupled to the body 14 of the laryngoscope 12 and/or to disable the advanced monitoring functions upon removal of the blade 28 (e.g., upon separation of the magnet 32 from the sensor 34 or upon loss of the signal from the sensor 34). For example, a processor of the laryngoscope 12 may be programmed to disable the monitoring functions in response to a loss of the signal from the sensor 34. In such cases, the medical professional may subsequently enable the advanced monitoring functions by coupling the activating blade 28 or another activating blade to the body 14 of the laryngoscope 12.

As noted above, it should be appreciated that the blade 28 may include any suitable activating element that is detectable by the sensor 34 of the body 14 of the laryngoscope 12. For example, the sensor 34 may include one or more magnetometers (e.g., proximity sensor, reed switch, Hall effect sensor) that are configured to detect the magnet 32. In another example, the sensor 34 may include one or more optical sensors (e.g., photodetector) configured to detect light, and the activating element on the blade 28 may include one or more obscure (e.g., non-transparent or light-reflecting) portions configured to block light from reaching the one or more optical sensors when the blade 28 is coupled to the body 14. In this case, when the blade 28 is attached to the laryngoscope 12, the sensor 34 is triggered by detecting a sudden decrease in the amount of light that reaches the sensor 34. In another example, the body 14 of the laryngoscope 12 may include a small light source, such as an LED, and the sensor 34 may include one or more optical sensors (e.g., photodetectors). In this case, when the blade 28 having one or more reflective surfaces is coupled to the body 14, the sensor 34 is triggered by detecting a sudden increase in the amount of reflected light that reaches the sensor 34. In another example, the blade 28 contains a small light source, such as an LED, and the sensor 34 is triggered by detecting a sudden increase in the amount of light that reaches the sensor 34. In another example, the sensor 34 may include one or more radio-frequency identification (RFID) readers, and the activating element may include one or more RFID tags readable by the one or more RFID readers when the blade 28 is coupled to the body 14. In another example, the sensor 34 may include one or more mechanical switches (e.g., physical buttons) positioned on the arm 24 of the body 14 of the laryngoscope 12, and the activating element may include one or more switch-actuating features (e.g., protrusions or prongs) configured to engage and to actuate the one or more mechanical switches when the blade 28 is coupled to the body 14. It should be appreciated that the blade 28 or any of the activating blades may include a combination of different activating elements, and the laryngoscope 12 may include multiple different types of sensors 34. For example, in some embodiments, the blade 28 may include one or more magnets 32 and one or more light-reflecting portions, and the laryngoscope 12 may include one or more magnetometer sensors 34 configured to detect the one or more magnets 32 and one or more optical sensors 34 configured to detect the light-reflecting portions. In this way, various types of activating elements and sensors may be used separately or in combination to selectively enable various monitoring functions.

In another embodiment, the activating element may include a visible marker or unique identifier that is marked on the blade 28 and that is visible to the camera 26 as the camera 26 passes into the blade 28. For example, the unique identifier could be a barcode, text (letters and/or numbers), or graphic (such as a symbol or QR code) that is marked, etched, printed, inked, molded, or otherwise formed on the blade. It is located on the activating blade 28 within view of the camera 26 as the camera 26 passes into the blade's interior channel, such as along the channel of the blade 28. In an embodiment, the unique identifier is not visible to the camera 26 once the camera 26 passes to the end of the channel, so that the unique identifier does not obscure the camera's field of view during operation of the laryngoscope 12. The controller on the laryngoscope 12 is programmed to recognize this identifier. If the laryngoscope 12 recognizes the unique identifier, the advanced monitoring functions are activated; otherwise, they are not. The unique identifier, once captured by the camera 26, is provided as part of camera data to a controller of the laryngoscope 12.

Furthermore, although only the activating blade 28 and the non-activating blade 70 are shown in FIG. 1 to facilitate discussion, it should be appreciated that the laryngoscope 12 may be utilized with one or more other types of blades. For example, in addition to or as an alternative to the activating blade 28 and the non-activating blade 70 shown in FIG. 1, the laryngoscope 12 may be utilized with a second activating blade that includes one or more magnets 32 (e.g., in a different position or having a different strength compared to the magnet 32 of the activating cover 28), an RFID blade that includes an RFID tag, an optical blade that includes light-reflecting portions, and/or a switch-actuating blade that includes a switch-actuating feature. In such cases, detection of the one or more magnets of the second activating blade, the RFID tag of the RFID blade, the light-reflecting portions of the optical blade, or the switch-actuating feature of the switch-actuating blade by respective sensors 34 of the body 14 of the laryngoscope 12 may enable different monitoring functions. For example, detection of the magnet 32 of the first blade 28 may activate a first set of advanced monitoring functions (e.g., data recording and data transfer), detection of the one or more different magnets 32 of the second blade may activate a second set of advanced monitoring functions (e.g., a subset of the first set, such as only data recording), and failure to detect any magnets 32 may block activation of the first and second sets of advanced monitoring functions. It should be appreciated that the laryngoscope 12 may be utilized with any number of different blades (e.g., 2, 3, 4, 5, or more) that have different types or configurations of activating elements (e.g., magnets, optical elements, RFID tags, switch-actuating features) to activate various advanced monitoring functions. Different types or configurations of activating elements may be used on a particular type of blade 28, and thus, detection of the different types or configurations of activating elements by the sensor 34 indicates to the laryngoscope 12 the type of blade 28 coupled to the body 14 of the laryngoscope 12. Furthermore, each type of blades 28 may enable different monitoring functions due to the different types or configurations of activating elements. For example, blades 28 having a particular shape may include one magnet 32 of a particular strength that enables a first set of advanced monitoring functions (e.g., data recording and data transfer), while blades 28 having another shape may include one magnet 32 of a different strength (e.g., unique strength) that enables a second set of advanced monitoring functions (e.g., a subset of the first set, such as only data recording).

It should be appreciated that the body 14 of the laryngoscope 12 may be reusable and the blades, such as the activating blade 28 and the non-activating blade 70, may be disposable (e.g., used one time and/or for a single patient). Thus, the body 14 may be used with multiple blades over time. With the foregoing in mind, in operation, the medical professional may select a desired blade (e.g., based on shape, size, features, monitoring functions enabled by the blade, etc.) and attach the selected blade to the body 14 of the laryngoscope 12. The medical professional may also power the laryngoscope 12 on via the power button 42. In certain embodiments, if the activating blade 28 is attached to the body 14, the sensor 34 will detect the magnet 32 and will generate a signal to instruct a processor of the laryngoscope 12 to enable the advanced monitoring functions. However, if the non-activating blade 70 is attached to the body 14, the sensor 34 will not detect the magnet 32 and the processor of the laryngoscope 12 will not enable the advanced monitoring functions. It should be appreciated that the laryngoscope 12 may not include a processor configured to carry out processing steps, such as processing images obtained by the camera 26 or enabling monitoring functions, but instead the laryngoscope 12 may have minimal or no processing power and may transmit raw data (e.g., ones and zeros) indicative of detection of the magnet 32 by the sensor 34 to the monitor 50. Furthermore, the sensor 34 may include a basic sensor or mechanical switch and/or detection of the magnet 32 by the sensor 34 may result in a relatively basic or mechanical response, such as a sound, that indicates to the medical professional that the magnet 32 is detected by the sensor 34. In such cases, various processing steps may be offloaded to the monitor 50 and/or the monitor 50 may initiate certain advanced monitoring functions in response to detection of the magnet 32 by the sensor 34. Such configurations may reduce the cost and complexity of the laryngoscope 12.

Additionally or alternatively, detection of the magnet 32 by the sensor 34 may activate an RFID reader (e.g., carried by the body 14 of the laryngoscope 12), which may then read/write information to an RFID tag carried by the blade 28. For example, the RFID reader reads the RFID tag carried by the blade 28 (e.g., to identify whether the blade 28 has been used before), writes information to the blade 28 (e.g., information related to use of the blade 28 or to label the blade 28 as used), and then turns off until activated again by detection of another magnet 32 by the sensor 34. Such a configuration facilitates tracking data related to use of the blades 28, while also limiting power used by the RFID reader as the RFID reader is only activated at certain times.

Figure 2:
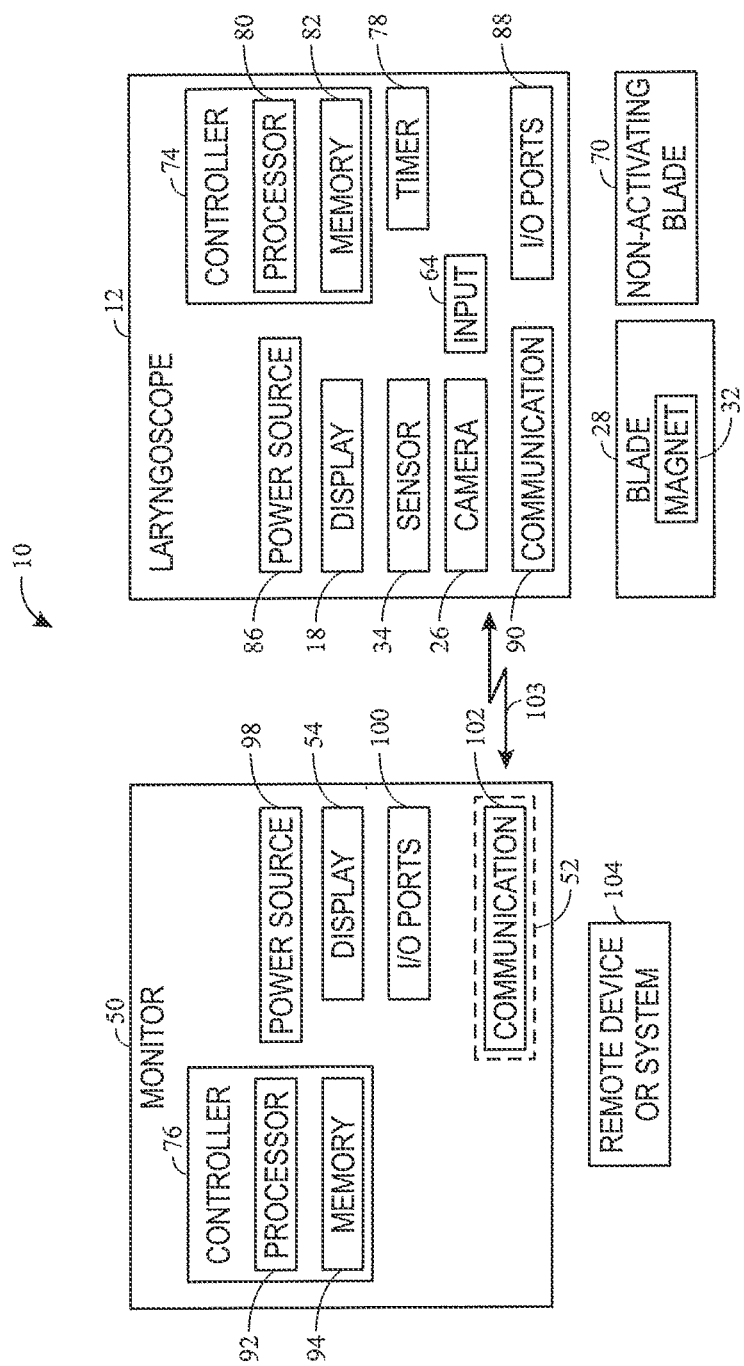
FIG. 2 is a block diagram of the laryngoscope system of FIG. 1, in accordance with an embodiment of the present disclosure.

FIG. 2 is a block diagram of an embodiment of the laryngoscope system 10. As shown, the laryngoscope system 10 includes the laryngoscope 12, which is configured to be coupled to the activating blade 28 having the magnet 32 or to the non-activating blade 70 that is devoid of the magnet 32 to form the laryngoscope 12. In certain embodiments, the laryngoscope system 10 may also include the monitor 50.

The laryngoscope 12 and the monitor 50 may include various components that enable the laryngoscope 12 to carry out the techniques disclosed herein. For example, the laryngoscope 12 may include the display screen 18, the camera 26, the sensor 34, and the input (e.g., touch sensor) 64, as well as a controller 74 (e.g., electronic controller), one or more processors 80, a hardware memory 82, a power source (e.g., battery) 86, input/output (I/O) ports 88, a communication device 90, and a timer 78. In some embodiments, the timer 78 may track relative time (e.g., a start time, an end time, a length of the monitoring session), which may be communicated to and/or used by the monitor 50 (e.g., in combination with data from a real-time clock of the monitor 50) to determine and/or associate a real time with the images obtained by the laryngoscope 12, for example. The monitor 50 may include the display screen 54, a controller 76 (e.g., electronic controller), one or more processors 92, a hardware memory 94, a power source (e.g., battery or input from external power source) 98, I/O ports 100, and a communication device 102. The power sources 86, 98 may be rechargeable and/or replaceable batteries. The communication devices 90, 102 may be wireless transceivers that are configured to establish wireless communication 103 with one another. By way of example, the communication devices 90, 102 may be configured to communicate using the IEEE 802.15.4 standard, and may communicate, for example, using ZigBee, WirelessHART, or MiWi protocols. Additionally or alternatively, the communication devices 90, 102 may be configured to communicate using the Bluetooth standard or one or more of the IEEE 802.11 standards. As noted above, in some embodiments, the communication device 90 may be provided in the adapter 52 that is configured to couple to the monitor 50 to facilitate wireless communication 103 between the laryngoscope 12 and the monitor 50.

In certain embodiments, the laryngoscope system 10 may include one or more remote devices or systems 104, such as computing systems (e.g., handheld or portable computing systems operated by the medical professional, such as a tablet, smart phone, or the like; hospital computing systems; or the like), room display systems, and/or hospital data storage systems. The remote devices or systems 104 may be configured to communicate (e.g., send and/or receive signals from) with the laryngoscope 12 and/or the monitor 50 via wireless or wired connections. For example, the laryngoscope 12 and/or the monitor 50 may relay the image data received from the laryngoscope 12 to the remote device or system 104 for display and/or storage.

In certain embodiments, the laryngoscope 12 and the monitor 50 include electrical circuitry configured to process signals, such as signals generated by the camera 26, signals generated by the sensor 34, and/or control signals provided via inputs, such as the inputs 58, 60 of the monitor 50, or the input 64 on the laryngoscope, for example. In the illustrated embodiment, the processors 80, 92 may be used to execute software. For example, the processor 80 of the laryngoscope 12 may be configured to receive signals from the camera 26 and to execute software to generate an image and/or to carry out any of a variety of processes in accordance with the present disclosure (e.g., display the image, store the image, transfer the image, or the like). Moreover, the processors 80, 92 may include multiple microprocessors, one or more "general-purpose" microprocessors, one or more special-purpose microprocessors, and/or one or more application specific integrated circuits (ASICS), or some combination thereof. For example, the processors 80, 92 may include one or more reduced instruction set (RISC) processors. It should be appreciated that the various processing steps may be carried out by either processor 80, 92 or may be distributed between the processors 80, 92 in any suitable manner.

The hardware memory 82, 94 may include a volatile memory, such as random access memory (RAM), and/or a nonvolatile memory, such as read-only memory (ROM). It should be appreciated that the hardware memory 82, 94 may include flash memory, a hard drive, or any other suitable optical, magnetic, or solid-state storage medium, other hardware memory, or a combination thereof. The memory 82, 94 may store a variety of information and may be used for various purposes. For example, the memory 82, 94 may store processor-executable instructions (e.g., firmware or software) for the processors 80, 92 to execute, such as instructions for processing signals generated by the camera 26 to generate the image, provide the image on the display screen 18, and/or transmit the image to the monitor 50. The hardware memory 82, 94 may store data (e.g., previously obtained images, time data, etc.), instructions (e.g., software or firmware for generating the images, storing the images, transmitting the images, etc.), and any other suitable data. As noted above, the activating blade 28 and the non-activating blade 70 are shown to facilitate discussion; however, it should be appreciated that the laryngoscope 12 may be utilized with any number of different blades (e.g., 2, 3, 4, 5, or more) that have different types or configurations of activating elements (e.g., magnets, optical elements, RFID tags, switch-actuating features) to enable various advanced monitoring functions.

Figure 3:
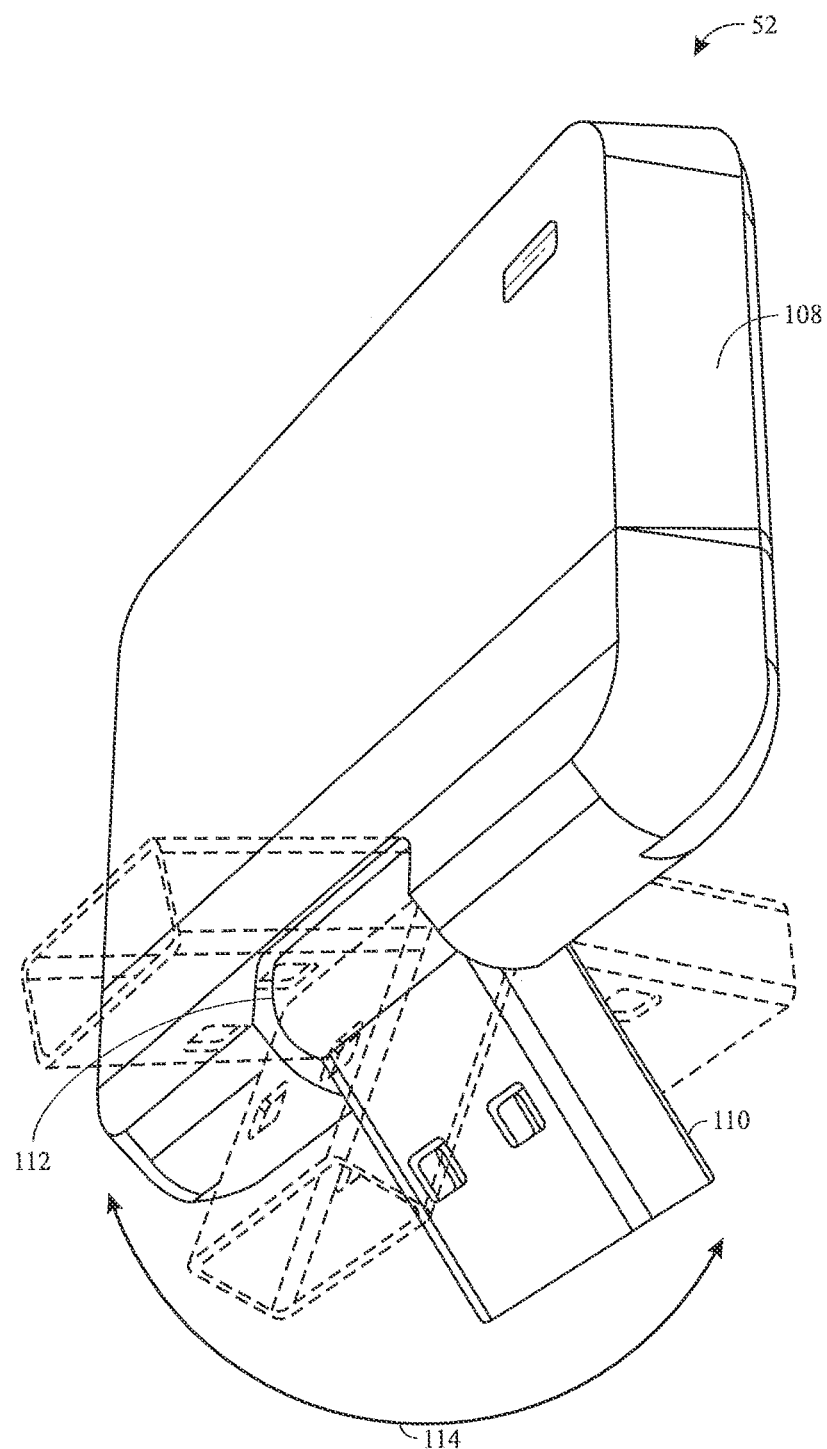
FIG. 3 is a perspective view of an adapter that is configured to facilitate wireless communication between a monitor and the laryngoscope of FIG. 1, in accordance with an embodiment of the present disclosure.

FIG. 3 is a perspective view of the adapter 52 that is configured to couple to the monitor 50 to facilitate wireless communication between the laryngoscope 12 and the monitor 50 and/or other remote devices and systems. In the illustrated embodiment, the adapter 52 is a dongle that includes a housing 108 that is configured to support electronic components (e.g., the communication device 102 of FIG. 2 and associated circuitry), and a connector 110 (e.g., USB connector, male connector) that is configured to couple to a corresponding connector (e.g., USB port, female connector) of the monitor 50 to relay information or commands between the laryngoscope 12 and the monitor 50. As shown, in some embodiments, the connector 110 is rotatably supported by a hinge 112 (e.g., rod or pivot), and the connector 110 is configured to rotate relative to the housing 108, as shown by arrow 114. The hinge 112 enable the housing 108 to sit flat against a surface of the monitor 50, thereby providing a low profile, reducing breakage of the adapter 52, and so forth. Such a configuration may enable the adapter 52 to be coupled to a variety of monitors, including third-party monitors or multi-parameter monitors, for example. In an embodiment, the dongle 52 connects to a monitor (e.g., the monitor 50), receives video or still images from the laryngoscope 12 wirelessly in substantially real-time, and provides those images to the monitor for display in substantially real-time during a medical procedure. In another embodiment, the dongle 52 receives video or still images from the laryngoscope 12 wirelessly during or after a medical procedure, and then, after the procedure is over, the dongle 52 is connected to another device (such as a laptop computer, monitor, or other computer system) to download the images into the patient's medical record or other electronic storage. This enables image data to be transferred from the video laryngoscope 12 to a patient's medical record (or other system), after a medical procedure is already over, and even when the laryngoscope 12 itself is devoid of any external (wired) ports.

Figure 4:
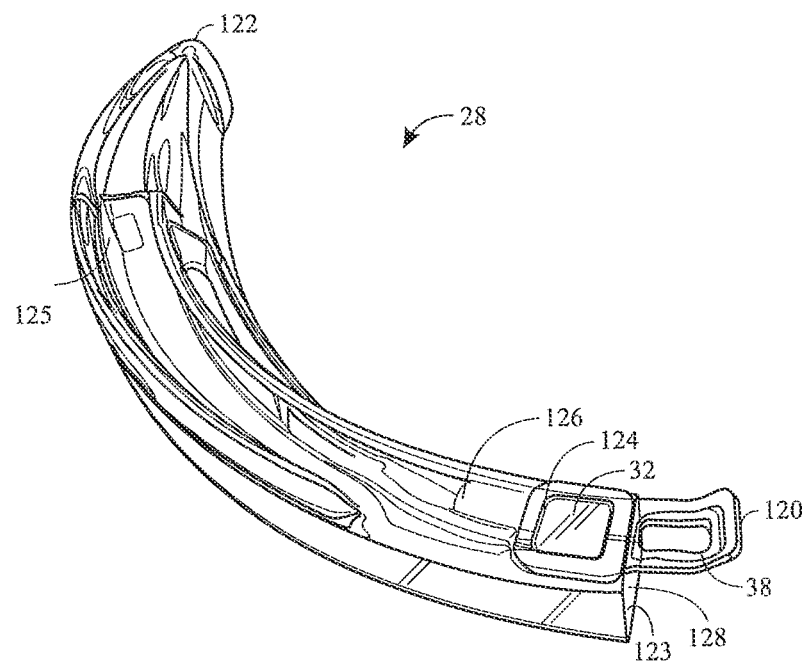
FIG. 4 is a perspective view of an activating blade that may be coupled to a body of the laryngoscope of FIG. 1, in accordance with an embodiment of the present disclosure.

FIG. 4 is a perspective view of an embodiment of the activating blade 28 that may be used as part of the laryngoscope 12. As shown, the blade 28 extends from a first end 120 (e.g., proximal end) to a second end 122 (e.g., distal end). The blade 28 includes an interior channel 128 that extends partially along a length of the blade 28 from a channel opening 123 proximate to the first end 120 to a channel terminus 125 (e.g., a closed end or end face). The arm 24 of the laryngoscope (e.g., camera stick or camera-supporting extension) supporting the camera 26 may be inserted through the channel opening 123 into the interior channel to position the camera 26 proximate to the channel terminus 125. While the illustrated blade 28 is generally curved between the first end 120 and the second end 122, it should be appreciated that the blade 28 may have any suitable shape or geometry (e.g., linear, straight, angled, bent, etc.) to facilitate the laryngoscopy procedure. In an embodiment, the blade 28 is a laryngoscope blade that has a specialized outer contour shaped to facilitate manipulation of the patient's oral anatomy to facilitate intubation of the patient with a tracheal tube. This manipulation may include lifting the patient's jaw, moving the tongue, and opening the larynx. Examples of suitable contours for this procedure include a generally curved blade (e.g., Macintosh blade) or a generally straight blade (e.g., Miller blade, Wisconsin blade, Robershaw blade).

In the illustrated embodiment, the magnet 32 is positioned within a recess 124 (e.g., groove or indentation) on an outer lateral side surface 126 of the blade 28, although any suitable number of magnets 32 (e.g., 1, 2, 3, 4, 5, 6, or more) may be provided in any of a variety of locations about the blade 28. In this embodiment, the magnet 32 is spaced apart from the sensor 34 (e.g., not in direct contact), and the side of the blade 28 itself sits between the magnet 32 and the sensor 34. In another embodiment, one or more magnets 32 may be provided on an inner side surface of the blade 28, such that the one or more magnets 32 face and/or directly contact the arm 24 when the blade 28 is coupled to the arm 24 of the body 14 of the laryngoscope 12. In some embodiments, the magnet 32 is coupled to the blade 28 via an adhesive. The magnet 32 may be positioned at or near the first end 120 (e.g., near the channel opening 123 of the blade 28). In certain embodiments, the magnet 32 is positioned between the channel opening 123 and the channel terminus 125.

As noted above, the activating element of the blade 28 may have various configurations. For example, in some embodiments, the blade 28 may include multiple magnets 32 positioned at different locations. In such cases, the advanced monitoring functions may be activated only upon detection of each of the multiple magnets 32 at the different locations by respective sensors 34. In certain embodiments, the blade 28 may include one or more magnets 32 having a particular magnetic field strength. In such cases, the advanced monitoring functions may be activated only upon detection by a sensor 34 of the one or more magnets 32 with the expected magnetic field strength (e.g., within an expected range). In certain embodiments, the blade 28 may include multiple magnets 32 at different locations and with different magnetic field strengths. In such cases, the advanced monitoring functions may be activated only upon detection of each of the multiple magnets 32 having the particular respective magnetic field strengths. As noted above, different types of activating elements may be used in combination. For example, in some embodiments, the blade 28 may include the magnet 32 and another type of activating element, such as a light reflecting portion that is detectable by an optical sensor on the body 14 of the laryngoscope 12, or and RFID tag that is detectable by an RFID reader on the body 14 of the laryngoscope 12. In some such cases, the advanced monitoring functions may be activated only upon detection of the multiple activating elements (e.g., upon detection of each of the magnet 32 and the light-reflecting portion or the RFID tag by respective sensors). Such configurations may advantageously reduce the incidence of inadvertent activation of the advanced monitoring functions. In some such cases, the advanced monitoring functions may be activated upon detection of only one of several activating elements (e.g., upon detection of any one of the magnet 32, the light-reflecting portion, or the RFID tag). Such configurations may advantageously provide redundancy in the event that one of the sensors 34 improperly fails to detect the corresponding activating element (e.g., one of the sensors 34 fails, one of the activating elements is damaged or is not aligned properly with the respective sensor 34).

The channel terminus 125 of illustrated blade 28 is formed from an optically transparent material to enable the camera 26 to obtain an image or a video of the patient's oral cavity and/or to enable lighted emitted by a light source positioned on the arm 24 of the body 14 of the laryngoscope 12 to illuminate the patient's oral cavity. The rest of the blade 28 may also be transparent, or at least a portion of the blade 28 may be formed from a non-transparent material. The transparent material is also rigid (e.g., plastic material, transparent acrylic, polymer material, non-metallic material). The illustrated blade 28 also includes the slot 38 that is configured to receive the key 40 of the body 14 of the laryngoscope 12, as shown in FIG. 1.

The blade 28 is slid over the arm 24 like a sleeve, prior to insertion of the insertion assembly into the patient's oral cavity. As discussed above, the arm 24 may be reusable and the blade 28 may be disposable, such that multiple blades 28 may be coupled to the arm 24 to treat multiple patients over time, with each blade being disposed after use to prevent cross-contamination or infection spread between multiple patients or caregivers. In operation, the arm 24 may be inserted into the channel opening 123 to couple the blade 28 that supports the magnet 32 to the body 14 that supports the sensor 34.

Figure 5:
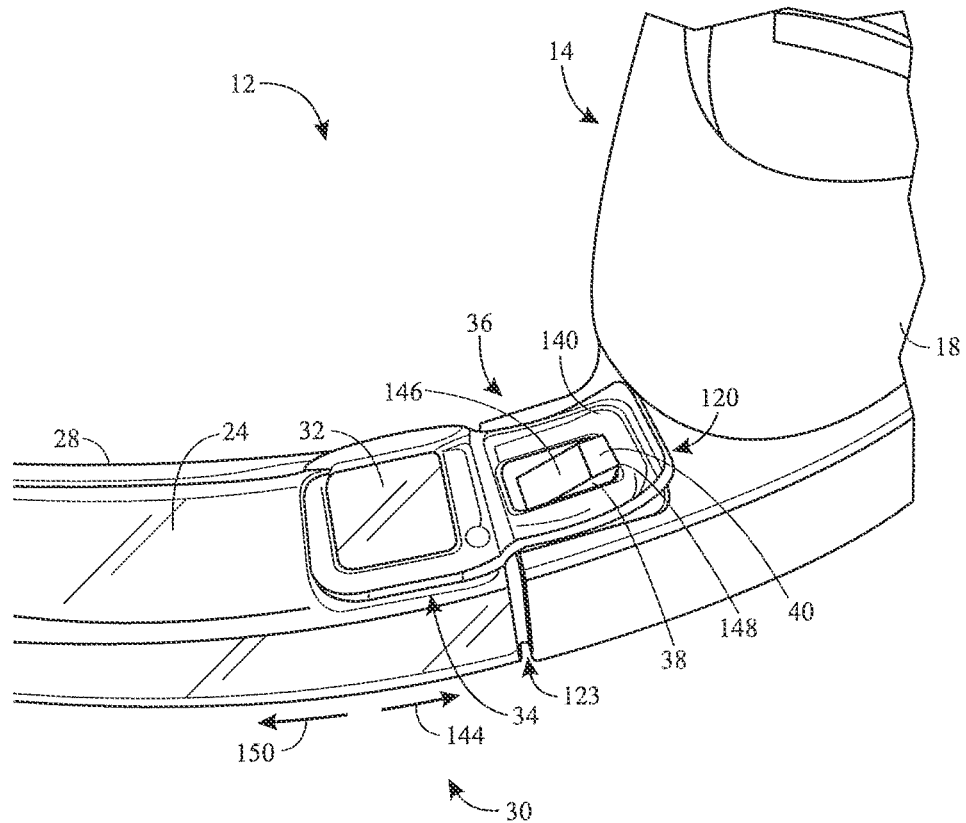
FIG. 5 is a perspective view of a coupling between the activating blade and the body of the laryngoscope of FIG. 1, in accordance with an embodiment of the present disclosure.

FIG. 5 is a perspective view of an embodiment of the coupling 36 between the blade 28 and the body 14 of the laryngoscope 12. In the illustrated embodiment, the coupling 36 is a latch, such as a key-slot interface with the slot 38 formed in a wing or tab 140 at the first end 120 of the blade 28, and the key 40 extends laterally-outwardly from the body 14 to engage the slot 38. Due at least in part to the geometry of the various components, the blade 28 may be attached to the body 14 by positioning the channel opening 123 proximate to the first end 120 of the blade 28 about the arm 24 of the body 14, and then sliding or driving the blade 28 toward the handle portion 20 of the body 14, as shown by arrow 144. The tab 140 may slide over a tapered surface 146 of the key 40 and then be held in place (e.g., an attached position) by a lip 148 of the key 40 extending through the slot 38. In certain embodiments, the blade 28 may be separated from the body 14 by lifting the tab 140 of the blade 28 (e.g., pulling the tab 140 laterally-outwardly over the key 40) and pulling the blade 28 away from the handle portion 20 of the body 14, as shown by arrow 150. In the illustrated embodiment, when the blade 28 is properly coupled to the body 14, the magnet 32 is positioned over the sensor 34. Thus, the coupling 36 is positioned to facilitate alignment between the magnet 32 and the sensor 34.

In some embodiments, the magnet 32 (or other activating element) may be positioned within the tab 140 of the blade 28, and the sensor 34 may be positioned proximate to the key 40. In such cases, sliding the slot 38 of the tab 140 over the key 40 may align the magnet 32 in the tab 140 with the sensor 34, thereby activating the advanced monitoring functions. As noted above, the activating element may have any of a variety of configurations, and in some cases may include a switch-actuating feature. In some such embodiments, the key 40 may include a mechanical switch, such that sliding the slot 38 of the extension portion 140 over the key 40 actuates the mechanical switch, thereby activating the advanced monitoring functions. In some such embodiments, the non-activating blade 70 may couple to the body 14 of the laryngoscope 12 via another type of coupling (i.e., the non-activating blade 70 may not include the slot 38 or may have a slot in a different location or with a different shape). As noted above, the illustrated coupling 36 is merely provided as an example, and it should be appreciated that the blade 28 and the body 14 may be joined together via any suitable coupling.

Figure 6:
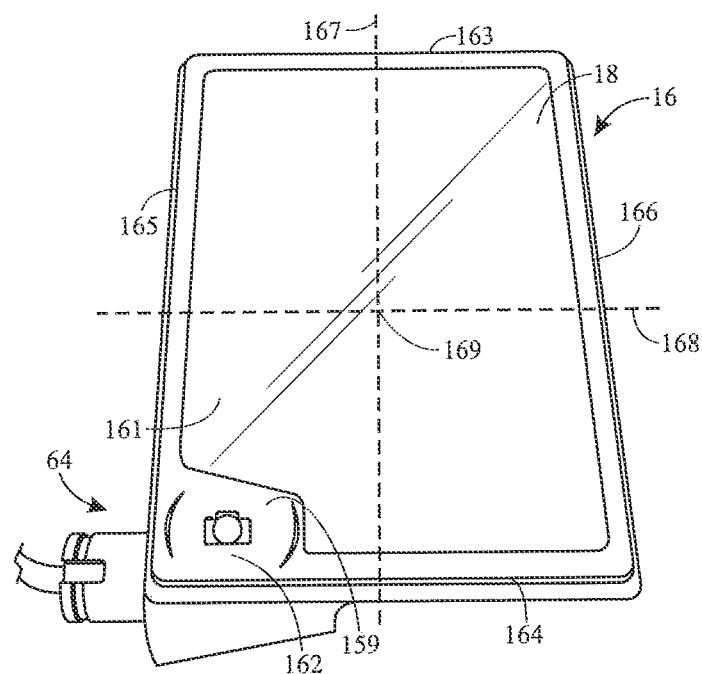
FIG. 6 is a front view of a display and a touch sensor input device that may be incorporated into the laryngoscope of FIG. 1, in accordance with an embodiment of the present disclosure.

FIG. 6 is a front view of an embodiment of the input 64 (e.g., capacitance sensor, touch sensor, pressure sensor, proximity sensor, or the like) that may be incorporated into the laryngoscope 12. In the illustrated embodiment, the input is a capacitive touch sensor 64 that is positioned behind a bezel or overlay 162 of the display screen 16, and the sensor 64 is configured to detect the presence of an object (e.g., a finger, stylus, or the like) at a region of the bezel 162 proximate to the sensor 64 and to generate a signal (e.g., input signal) in response to detection of the presence of the object. The input signal may be provided to the processor 80 of the laryngoscope 12. In some embodiments, various types of input signals may cause various responses or actions. For example, one type of touch (e.g., a single tap) detected by the touch sensor 64 may cause the processor 80 to instruct the camera 26 to take, store, or transmit a still image (e.g., capture and store the still image as a separate file in the local hardware memory 82). For example, another type of touch (e.g., a double tap or a press-and-hold for a certain time period) detected by the touch sensor 64 may cause the processor 80 to start or stop streaming a video to the monitor 50 and/or to transfer a video to the monitor 50. Such a configuration may enable the medical professional to efficiently provide an input to capture still or video images, transfer images, or carry out other various monitoring functions with the laryngoscope 12.

In some embodiments, the touch sensor 64 may be used to provide input to the processor 80 only after the advanced monitoring functions are enabled (e.g., detection of the magnet 32 enables operation of the touch sensor 64). If advanced monitoring functions are not enabled, the touch sensor 64 is disabled during use of the laryngoscope 12. In some embodiments, the processor 80 operates the touch sensor 64 to provide a first type of input (e.g., tap to zoom in or out) in the absence of detection of the magnet 32 and to provide an additional type of input (e.g., tap-and-hold to start or stop transmitting video) if the advanced monitoring functions are enabled due to detection of the magnet 32. It should be appreciated that additionally or alternatively the laryngoscope 12 may include other input devices (e.g., physical buttons or virtual buttons on the touchscreen display screen 18) to enable the medical professional to provide such inputs.

In the illustrated embodiment, the bezel 162 includes a single-piece frame that circumferentially surrounds the display screen 18 (e.g., covers and protects edges of the display screen 18) and that has an enlarged corner or wing 159 that overlays the touch sensor 64. The display portion 16 includes an upper edge 163, a lower edge 164, a left edge 165, and a right edge 166. The upper edge 163 is distal from the handle portion 20 (FIG. 1) and the lower edge 164 is proximate to the handle portion 20 (FIG. 1), and the left edge 165 is on the left-hand side and the right edge 166 is on the right-hand side relative to the medical professional holding the laryngoscope 12 during the laryngoscopy procedure. The display portion 16 may be divided into quadrants by a vertical axis 167 and a lateral axis 168 that are orthogonal to one another and intersect at a center 169 of the display portion 16. As shown, the touch sensor 64 is positioned in a lower left quadrant 161 of the display portion 16 defined between the lower edge 164, the left edge 165, the vertical axis 167, and the lateral axis 168 and is proximate to a lower left corner of the display screen 18, as this location is unlikely to block key anatomical features in the image shown on the display screen 18 during an intubation. In some embodiments, the touch sensor 64 (or other input devices on the display portion 16 of the laryngoscope 12) is positioned between the left edge 165 and the vertical axis 167, between the lower edge 164 and the lateral axis 168, in the lower left quadrant 161, or in any other suitable location that does not block visualization of key anatomical features in the image shown on the display screen 18. The lower left quadrant 161 may also be a convenient location for the touch sensor 64, as this location may be reached by the medical professional's thumb (e.g., to provide inputs via touch of the thumb to a touch sensing zone of the touch sensor 64) while the medical professional holds the handle portion 20 of the laryngoscope 12. It should be appreciated that the bezel 162 may have any suitable form and that any suitable number of touch sensors 64 (e.g., 1, 2, 3, 4, 5, or more) and/or other input devices may be provided at any of a variety of locations about the body 14 of the laryngoscope 12. The illustrated configuration provides a durable touch sensor 64 that may advantageously be submerged in water and/or subject to gas during cleaning of the laryngoscope 12.

Figure 7:
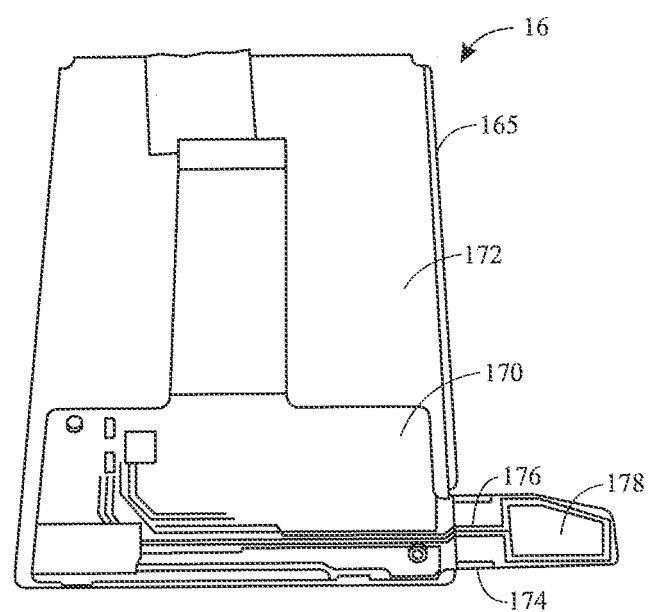
FIG. 7 is a rear view of a display portion of the laryngoscope of FIG. 1 during assembly of the touch sensor input device of FIG. 6, in accordance with an embodiment of the present disclosure.
Figure 8:
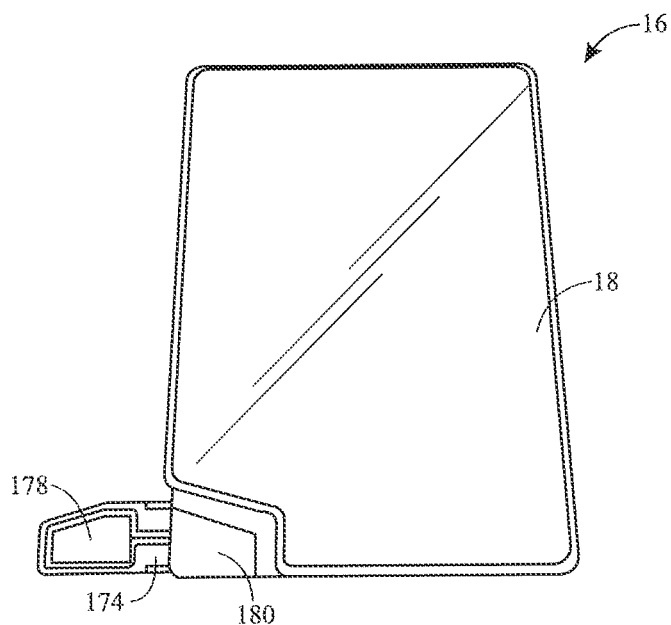
FIG. 8 is a front view of the display portion of FIG. 7 during assembly of the touch sensor input device of FIG. 6, in accordance with an embodiment of the present disclosure.
Figure 9:
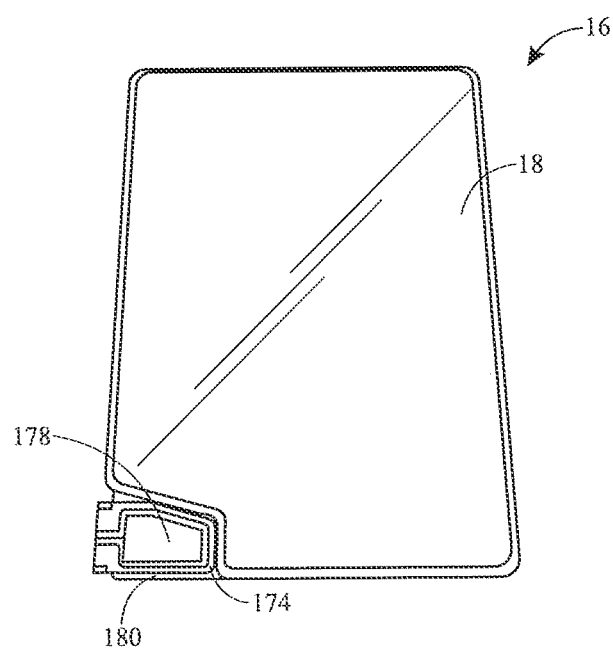
FIG. 9 is a front view of a portion of the touch sensor input device of FIG. 6 positioned on a front side of the display portion of FIG. 7, in accordance with an embodiment of the present disclosure.

FIGS. 7-9 illustrate an embodiment of a process for incorporating the touch sensor 64 into the laryngoscope 12. As shown in FIG. 7, the display portion 16 of the body 14 of the laryngoscope 12 includes a flexible circuit 170. In the illustrated embodiment, the flexible circuit 170 is attached (e.g., adhered) to a rear side of a frame 172 (e.g., support structure or housing) of the display portion 16, and a tab 174 (e.g., flap) of the flexible circuit 170 extends (e.g., laterally-outwardly) from the flex circuit 170 past the edge of the frame 172. The tab 174 may include conductive circuitry 176 that electrically couples a touch sensing zone 178 (e.g., capacitance sensor, electrodes, etc.) to a processing device, such as the processor 80.

As shown in FIG. 8 and FIG. 9, in an embodiment, the tab 174 folds or bends around an edge (e.g., the left edge 165) of the frame 172 to position the touch sensing zone 178 of the tab 174 on a front side of the frame 172. In the illustrated embodiment, the tab 174 fits within a recess 180 of the frame 172. The display screen 18 may have a cutout corner around the recess 180, or the recess 180 may be formed as a recessed or indented area of the display screen 18 itself. The tab 174 may be attached to the recess 180, such as via an adhesive, for example. Once the tab 174 is positioned in the recess 180, the bezel 162 may be mounted to the frame 172 with the wing 159 covering the tab 174, thereby forming the display portion 16 having the touch sensor 64 located in the lower left quadrant 161, as shown in FIG. 6. Thus, the tab 174 is sandwiched between the bezel 162 and the frame 172, or between the bezel 162 and the glass surface of the display screen 18. The wing 159 is shaped to correspond to the sensing zone 178 of the touch sensor 64, and the touch sensor 64 is calibrated to detect a touch to the front surface of the wing 159, through the thickness of the bezel 162. This structure gives a clear indication to the user where to touch the screen 18 in order to provide an input. In some embodiments, the display screen 18 is non-interactive (e.g., is not a touch screen, and is not configured to receive inputs via touch, pressure, or proximity), and instead, the laryngoscope 12 may receive inputs via touch only at the wing 159 (the portion of the bezel 162 that covers the touch sensing zone 178). The front surface of the wing 159 is identified by the camera icon in FIG. 6. In this embodiment, the display screen 18 behaves as a touch screen in the sensing zone 178, even though the display screen 18 is non-interactive. That is, outside of the sensing zone 178, the display screen 18 does not interact with the user (e.g., is not responsive to touch or proximity inputs). This structure enables the display screen 18 to behave like a touch screen in the one area (the sensing zone 178) that is easily reached by the user's thumb, so the screen 18 can be operated easily by a user who is familiar with touch screens. However, the screen 18 can also be wiped clean or handled (away from the sensing zone 178) without triggering the touch sensor 64 and without causing any inadvertent inputs. The display screen 18 is durable and easily cleanable, and yet it gives the user an intuitive touch input in the zone 178 of the touch sensor 64.

Figure 10:
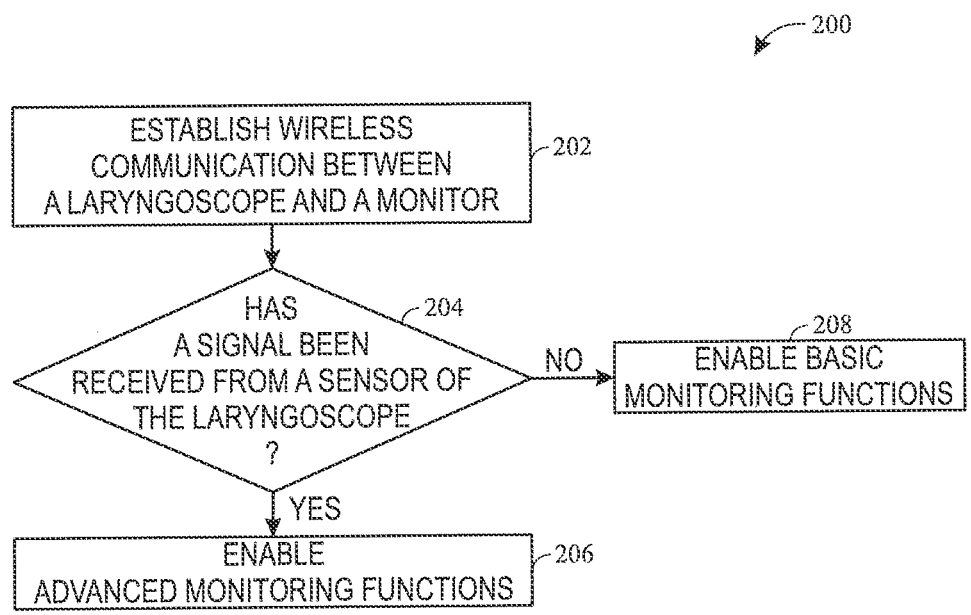
FIG. 10 is a process flow diagram of a method of using the laryngoscope system of FIG. 1, in accordance with an embodiment of the present disclosure.

FIG. 10 is a process flow diagram of a method 200 of using the laryngoscope system 10 of FIG. 1, in accordance with an embodiment of the present disclosure. The method 200 disclosed herein includes various steps represented by blocks. It should be noted that at least some steps of the method 200 may be performed as an automated procedure by a system, such as laryngoscope system 10. Although the flow chart illustrates the steps in a certain sequence, it should be understood that the steps may be performed in any suitable order and certain steps may be carried out simultaneously, where appropriate. Additionally, steps may be added to or omitted from of the method 200. Further, certain steps or portions of the method 200 may be performed by separate devices. For example, a first portion of a method 200 may be performed by the processor 80 of the laryngoscope 12, while a second portion of the method 200 may be performed by the processor 92 of the monitor 50. In addition, insofar as steps of the method 200 disclosed herein are applied to received signals, it should be understood that the received signals may be raw signals or processed signals. That is, the method 200 may be applied to an output of the received signals.

With the foregoing in mind, the method 200 of FIG. 10 may begin with establishing wireless communication between the laryngoscope 12 and the monitor 50, in step 202. As discussed above, the medical professional may turn the laryngoscope 12 on via the power button 42 and may turn the monitor 50 on via the power button 62. In some embodiments, once powered on, the laryngoscope 12 and the monitor 50 may automatically establish wireless communication with one another. In some embodiments, the laryngoscope 12 and/or the monitor 50 may provide an indication (e.g., via respective display screens 18, 54) upon establishing wireless communication with one another. In some embodiments, the laryngoscope 12 may display a monitor ID of the connected monitor 50 on the display screen 18 and/or the monitor 50 may display a laryngoscope ID of the connected laryngoscope 12 on the display screen 54. In some embodiments, the medical professional may provide inputs (e.g., via touchscreen display screens 18, 54) to adjust or to select the appropriate device(s) (e.g., the monitor 50 or the laryngoscope 12) that should communicate with one another during the laryngoscopy procedure. It should be appreciated that other remote devices and systems 104 may be powered on and/or communicatively coupled to the laryngoscope 12 and/or the monitor 50 in the same manner.

In step 204, the processor 80 of the laryngoscope 12 determines whether a signal from the activating element (e.g., the magnet 32) has been received at the processor 80. For example, in response to detection of the activating element of the blade 28, the sensor 34 may generate a signal that is transmitted to the processor 80.

In step 206, the processor 80 may enable advanced monitoring functions, such as recording data (e.g., images, time data, or the like) and/or transfer of data to another device (e.g., the monitor 50 or the remote device or system 104) in response to receipt of the signal from the sensor 34. For example, in response to receipt of the signal, the processor 80 may begin automatically recording data (e.g., image or time data) and storing it on the laryngoscope 12 (e.g., in the hardware memory 82). In some embodiments, in response to receipt of the signal and receipt of an input from the medical professional (e.g., a touch-and-hold input at touch sensor 64 of the laryngoscope 12 and/or a touch input on the monitor 50), the processor 80 of the laryngoscope 12 may begin transferring images (e.g., streaming video) to the monitor 50 and/or to another remote device and system 104. In some embodiments, in response to response to receipt of the signal and receipt of an input from the medical professional (e.g., a touch input at touch sensor 64 of the laryngoscope 12 and/or a touch input on the monitor 50) and/or at certain times (e.g., upon powering the laryngoscope 12 and/or the monitor 50 off or on, periodically during the laryngoscopy procedure, upon receipt of an input indicating that the laryngoscopy procedure is complete and/or that certain steps of the laryngoscopy procedure are complete), the processor 80 of the laryngoscope 12 may initiate a transfer of data (e.g., from the hardware memory 82) to the monitor 50 and/or to the remote storage device or system 104. For example, upon receipt of an input at the power button 42 to power off the laryngoscope 12, the processor 80 may, prior to powering off the laryngoscope 12, stop recording data locally, stop providing the image on the display screen 18, and/or transfer recorded data (e.g., images and time data recorded after detection of the activating element by the sensor 34 in step 204) from the hardware memory 82 to the monitor 50. In some embodiments, the processor 80 may provide an indication (e.g., via the display screen 18) of the data transfer operation to the monitor 50 and/or the progress of the data transfer to the monitor 50. In some embodiments, the data that is transferred from the laryngoscope 12 to the monitor 50 and/or to the remote device or system 104 is not associated with a patient-identifying information. That is, the laryngoscope 12 does not maintain patient-identifying information, but instead, merely transfers the data to the monitor 50 and/or to another remote device or system 104 where the data may then be associated with patient-identifying information and/or linked to records for a particular patient. Such a configuration may simplify the data transfer process, for example.

In some embodiments, the data recorded on the laryngoscope 12 may be accessed by the monitor 50 and/or the remote device or system 104 at a later time or during a subsequent session (e.g., after the laryngoscope 12 is powered off and then on again). Such a configuration may preserve the data for later access and/or transfer in the event that the data cannot be transferred to the monitor 50 and/or the remote device or system 104 during the laryngoscopy procedure (e.g., due to an interruption in wireless communication), for example. The image data may be time-stamped or otherwise indexed or ordered so that the image data can be sent to the appropriate patient file, in the event that two or more different patients are imaged with the laryngoscope 12 before the image data is transferred. In some embodiments, the data may be automatically deleted from the laryngoscope 12 after a predetermined period of time (e.g., 1, 2, 3, 4, 5, 6, 7, or more days). The predetermined period of time may vary based on whether the data has been transferred to the monitor 50 and/or the remote device or system 104. For example, the data may be deleted after 2 days if the data was transferred to the monitor 50 and/or the remote device or system 104, but may be deleted after 7 days if the data was transferred to the monitor 50 and/or the remote device or system 104. It should be appreciated that the data may be deleted from the laryngoscope 12 automatically after transfer to the monitor 50 and/or the remote device or system 104 and/or the data may be stored on the laryngoscope 12 until the data is transferred to the monitor 50 and/or the remote device or system 104. In some embodiments, after the processor 80 enables the advanced monitoring functions and/or provides instructions to carry out the advanced monitoring functions, the medical professional may provide an input to stop one or more of the advanced monitoring functions. For example, the medical professional may provide an input via the laryngoscope 12 and/or the monitor 50 (e.g., the touch sensor 64 and/or the inputs 58, 60) that causes the processor 80 to stop recording data and/or to stop transferring (e.g., streaming) data to the monitor 50. As noted above, in some embodiments, the laryngoscope 12 may be utilized with multiple different types of blades having various activating elements that may enable various monitoring functions (e.g., different sets of functions).

In step 208, if the processor 80 does not receive the signal from the sensor 34, the processor 80 does not enable advanced monitoring functions, and instead enables relatively basic functions (e.g., different functions and/or fewer functions). Thus, upon coupling the non-activating blade 70 to the body 14 of the laryngoscope 12, the advanced monitoring functions are not enabled and the laryngoscope 12 may carry out the relatively basic functions, such as obtaining images using the camera 26 and displaying the images obtained by the camera 26 on the display screen 18 of the laryngoscope 12, for example.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:
1. A laryngoscope system, comprising:
a removable blade comprising an activating element; and
a laryngoscope, comprising:
 a body comprising a handle and an arm;
 a camera mounted on or near a distal end of the arm and configured to obtain image data;
 a display screen coupled to the body and configured to display the image data;
 a touch sensor coupled to the body and configured to generate a touch signal; and a processor disposed in the body and programmed to:
   absent detection of the activating element, operate the camera to obtain the image data and display, on the display screen, the image data; and
   in response to detection of the activating element, activate the touch sensor and enable at least one additional monitoring function in response to receipt of the touch signal.

2. The laryngoscope system of claim 1, wherein the at least one additional monitoring function comprises transfer of at least some of the image data to a device that is physically separate from the laryngoscope, storage of the at least some of the image data in a memory of the laryngoscope, or both.

3. The laryngoscope system of claim 1, wherein the processor is programmed to:
   operate a first function of the at least one additional monitoring function in response to a first type of touch signal; and
   operate a second function of the at least one additional monitoring function in response to
   a second type of touch signal.

4. The laryngoscope system of claim 1, wherein the laryngoscope is configured to detect the activating element with the camera or with a blade sensor disposed in the body of the laryngoscope.

5. The laryngoscope system of claim 1, wherein the laryngoscope comprises a blade sensor disposed in the body, and the activating element comprises a magnet detectable by the blade sensor.

6. The laryngoscope system of claim 1, wherein the laryngoscope comprises a housing that includes the display screen and a bezel that surrounds the display screen, and the touch sensor is located in a lower left quadrant of the housing.

7. The laryngoscope system of claim 6, wherein the display screen is non-responsive to touch and the touch sensor is positioned at the bezel.

8. The laryngoscope system of claim 1, wherein the touch sensor is one of a touchscreen of the display screen or a sensor separate from the display screen.

* * * * *